US 6,589,144 B1

(12) United States Patent
Ebihara et al.

(10) Patent No.: US 6,589,144 B1
(45) Date of Patent: Jul. 8, 2003

(54) DENTAL AUTOMATIC CUTTING APPARATUS

(75) Inventors: Yoshinori Ebihara, Tokyo (JP); Tokichi Shimizu, Kiryu (JP)

(73) Assignee: GC Corporation, Tokyo (JP)

( * ) Notice: Subject to any disclaimer, the term of this patent is extended or adjusted under 35 U.S.C. 154(b) by 221 days.

(21) Appl. No.: 09/661,443

(22) Filed: Sep. 13, 2000

(30) Foreign Application Priority Data

Sep. 14, 1999 (JP) ............................................ 11-260983
Sep. 20, 1999 (JP) ............................................ 11-265669
Aug. 29, 2000 (JP) ........................................ 2000-259147

(51) Int. Cl.$^7$ .......................... B23Q 3/157; B23Q 3/155
(52) U.S. Cl. ............................. 483/55; 483/54; 483/59; 483/58; 483/65; 483/69; 483/7
(58) Field of Search ............................ 483/55, 54, 59, 483/58, 65, 69, 7, 10, 12, 13

(56) References Cited

U.S. PATENT DOCUMENTS

| 4,520,551 A | | 6/1985 | Imhof |
| 4,658,493 A | * | 4/1987 | Saeki et al. .................. 483/66 |
| 4,658,494 A | | 4/1987 | Ohtani et al. |
| 5,688,215 A | * | 11/1997 | Mase et al. .................. 483/66 |
| 5,769,768 A | | 6/1998 | Polacek et al. |
| 5,885,199 A | * | 3/1999 | Shao ........................... 29/27 C |
| 6,113,322 A | * | 9/2000 | Harmand et al. ............ 409/132 |

FOREIGN PATENT DOCUMENTS

| EP | 0 371 890 | | 6/1990 | |
| GB | 2251565 A | * | 7/1992 | ............ B23B/47/28 |

* cited by examiner

Primary Examiner—William Briggs
Assistant Examiner—Dana Ross
(74) Attorney, Agent, or Firm—Oblon, Spivak, McClelland, Maier & Neustadt, P.C.

(57) ABSTRACT

A dental automatic cutting apparatus is disclosed, having a construction in which cutting tools are made automatically detachable to a chuck and a tool cassette by automatic control mechanism comprising: an engagement means provided to the tool cassette and a base block to maintain the tool cassette in a detachable manner to the base block to a desired position relation, the tool cassette provided on its front surface side with at least two post-inserting bore through which each tool post having a function to accommodate and hold the cutting tool which can be inserted, and the base block is fixed to a main body of the dental automatic cutting apparatus, and connection means for connecting the engagement means provided in the tool cassette to the base block to fix the tool cassette. In the dental automatic cutting apparatus of the invention, which is used for preparing dental prostheses such as crowns and inlays in a processing process by CAD/CAM, tool cassettes accommodating a plurality of types and/or a plural number of cutting tools can be made automatically detachable in a desired position.

3 Claims, 4 Drawing Sheets

DENTAL AUTOMATIC CUTTING APPARATUS

BACKGROUND OF THE INVENTION

1. Field of the Invention

The present invention relates to a dental automatic cutting apparatus that is used for preparing, through cutting processing, dental prostheses for undergoing prosthesis of missing teeth in an oral cavity of a patient, such as crowns and inlays, and particularly, to a dental automatic cutting apparatus in which a tool cassette accommodating plural kinds of and/or a plural number of cutting tools is detachable in a desired position.

2. Description of the Related Art

Dental prostheses for undergoing prosthesis of missing teeth in an oral cavity of a patient, such as crowns and inlays (the dental prosthesis or prostheses being sometimes referred to simply as "prosthesis" or "prostheses", hereinafter), are required to have a severe fitting precision. Accordingly, it has hitherto been commonly employed to prepare the prostheses by a precision casting process such as a lost wax process. Further, during the preparation of these prostheses, it was considered to be necessary to take a number of steps starting from preparation of a cavity as a prosthetic part by a dentist and inclusive of impression taking (molding) of the missing part and preparation of a gypsum model. Moreover, since, as described above, a severe fitting precision is required for the preparation of the prostheses, it is legally regulated within Japan that a person having a national qualification, called as a dental technician, must deal with it.

Now, with the progress of a computer technology in recent years, processing technologies with the computer technology as a nucleus are developing in various fashions. Such technologies are a processing technology generally called as CAD (computer aided design) and CAM (computer aided manufacturing). The application of the processing technology by CAD/CAM is being also attempted in various objects for preparing such prostheses in the dental field as described above.

For example, the technology as disclosed in Japanese Patent Laid-Open No. 187802/1983 is one example thereof, and the disclosed technology includes contents called as a digital type processing process by computer control. Specifically, this technology is concerned with a technology in which, by using a non-contact type reader utilizing a light wave or an acoustic wave, a shape of the prosthesis is read, the obtained data are converted into a digital signal, the signal is then sent to a digital control type machine tool, thereby preparing a prosthesis that is precisely fitting to the subjected body part (prosthetic part). These matters are automatically effected by a computer.

As the digital control type machine tool as exemplified herein, a micro slicing machine can be exemplified. As devices that can be used for processing small workpieces required to have a high precision, such as prostheses, a group of machine tools generally called as a machining center (the digital control type machine tool being sometimes referred to simply as "processing apparatus", hereinafter) is being used with the progress of machine tools in recent years.

Under such circumstances, in order to prepare effectively prostheses having a high precision, various devices have been attempted with respect to the mechanism of the apparatus itself as well as the material subjected to the cutting processing and cutting tools. For example, as a device for the processing apparatus itself, there is an application to a small-sized processing apparatus with an automatic opening and closing mechanism using a compressed air of a spindle chuck. Hitherto, the automatic opening and closing mechanism using a compressed air of a spindle chuck gripping a cutting tool could be installed only in a large-sized processing apparatus because of complexity of its construction. However, by applying various devices, it has become possible to install it even in a small-sized apparatus.

Further, an object for performing the preparation of a prosthesis by CAD/CAM resides in the matter that prostheses having a high dimensional precision as a single product are respectively prepared so as to be fitting to the shape of a part to be installed (a missing tooth of a patient) and that a large number of prostheses having various shapes can be continuously and simply prepared without giving troubles. In order to achieve this object, with respect to the material, a semi-product close to the shape and size of a prosthesis to be prepared, for example, one having a shape of column or rectangle (such semi-product being sometimes referred to simply as "semi-product", hereinafter), is prepared in advance.

And, examples of materials for the semi-product include from relatively soft ones such as dental noble metal alloys to rigid ones such as dental titanium alloys as well as from molded ones with a relatively good precision, which can be readily cut, such as dental synthetic resins (generally called as "dental composite resins" but sometimes called simply as "resins") to ones that are relatively inaccurate in size because of their properties and are hardly subjected to cutting processing, such as dental ceramics.

Now, under conditions in which such various materials are used as the semi-product, in order to subject the semi-product to cutting processing into a prosthesis having a desired shape, a processing in which by gripping a cutting tool at the tip of a spindle, shaping is carried out by rotating cutting is generally employed. For this purpose, it is a necessary condition for performing the processing with a good efficiency and a high precision that the cutting contents are previously designed and that cutting tools suitable for the cutting contents are prepared. This is because there is a background that because of differences in rough cutting or finish cutting fine cutting) or the like in terms of the cutting contents, differences in hardness due to a difference of the material, and deterioration in sharpness of a cutting edge of the cutting tools caused by cutting a number of semi-products, it is necessary to appropriately exchange the cutting tool from the standpoints to maintain processing efficiency and processing precision.

In this connection, the cutting tools used in the dental CAD/CAM will be described below in a little more detail. For the dental ceramics or dental composite resins to be used as a prosthetic material, use of a diamond cutter is preferred; and for processing of dental metals, particularly processing of dental titanium alloys, use of a carbide cutter is preferred. And, for example, when one wishes to obtain a whole of a part corresponding to an upper portion of a tooth (such a processed material being sometimes referred to simply as "crown", hereinafter) as a prosthesis through processing, while gripping the cutting tools, he or she must selectively use some cutting tools among those having different tip sizes and shapes as prepared taking into consideration purposes.

With respect to the prosthesis, in the case of the above-described crown, there are two types of those for a posterior tooth and an anterior tooth. On the other hand, there is also a prosthesis called as "inlay", which is used for filling a cavity formed by cutting off a tooth portion where a dental caries has been generated. The inlay includes a number of variations in terms of the size and shape such that it is not too much to say that there is nothing at all that has the same size and shape. In order to subject such an inlay to processing with a good precision, one must previously choose cutting tools having a size and a shape suitable for a shape to be cut. The thus previously chosen cutting tools are gripped by a chuck provided in a spindle and fixed by an operator personally in accordance with the progress of the cutting works.

However, if the cutting tools are replaced manually one by one, even when the automatic cutting processing is realized expressly by computer control, the working is interrupted on each occasion. Accordingly, not only the cutting works are inefficient, but also the complication for a worker is not solved. Thus, it is hard to say that benefits by the computer control are thoroughly utilized.

In order to overcome such inefficient and complicated matters, it may be considered to align a spindle for gripping a necessary number of cutting tools as expected. In other words, by employing such construction, cutting tools each having a size and a shape as expected are first set (gripped) in respective spindles and left to the automatic control by a computer until the completion of cutting. In this case, since the cutting works are not interrupted, not only the working efficiency is improved, but also a worker is liberated from the complication in exchange of the cutting tools.

However, the above-described construction involves new problems that not only the apparatus becomes large in size, but also the apparatus cost increases. In other words, if the number of spindles increases, the spindles must be subjected to position fitting, resulting in a non-negligible problem from the viewpoint of precision. And, after all, since it is impossible to use a plurality of spindles at once (the prosthesis is subjected to the processing and is extremely small, and such becomes a bottle-neck), this construction does not contribute to a reduction in the processing time so much. Rather, a risk of accident will increase in proportion to an increase in the number of the constructing members.

Accordingly, it is self-explanatory that when a construction in which at most two spindles are aligned is employed so as to make the whole of the apparatus small in size as far as possible, and the exchange of the cutting tools is automatically carried out by the control of a computer incorporated in the processing apparatus, the workability is largely improved. But, in order to choose suitable cutting tools depending on the progress of the cutting works, not only a vast and complicated program for computer control is necessary, but also a high-level technology for making a machine judge is involved. Accordingly, these requirements cannot be met at a current technical level. Therefore, realization of a processing apparatus in which desired cutting tools are automatically exchanged in a simpler construction and a human help is not substantially required has been demanded.

SUMMARY OF THE INVENTION

The present invention is aimed to provide a dental automatic cutting apparatus that is used for preparing dental prostheses such as crowns and inlays in a processing process by CAD/CAM and in which cutting tools are made automatically detachable to a chuck and a tool cassette by automatic control mechanism, wherein a necessary cutting tool is automatically gripped by or taken out from a chuck of a spindle from or to the tool cassette depending on the processing order by automatic control mechanism aligned in the processing apparatus, and the tool cassette set with necessary cutting tools as previously expected can be position-fixed simply and precisely to a predetermined position on the processing apparatus.

We, the present inventors made extensive and intensive investigations in order to overcome the above-described problems of the related art. As a result, we have invented a dental automatic cutting apparatus having a construction in which cutting tools are made automatically detachable to a chuck and a tool cassette by automatic control mechanism comprising: an engagement means provided to the tool cassette and a base block to maintain the tool cassette in a detachable manner to the base block to a desired position relation, the tool cassette provided on its front surface side with at least two post-inserting bores through which each tool post having a function to accommodate and hold the cutting tool which can be inserted, and the base block is fixed to a main body of the dental automatic cutting apparatus; and a connection means for connecting the engagement means is provided in the tool cassette to the base block to fix the tool cassette.

And, the inventors have found that, in the above-described construction, it is preferred that at least one proximity sensor is aligned in a predetermined position on the base block in the side to which the tool cassette is fixed, and the proximity sensor discriminates the type of a signal imparted to the fixed tool cassette; the engagement means is a bore formed by combining a cassette-fixing pin vertically provided on a rear surface side of the tool cassette, a groove bored on an upper surface of the base block, and a groove bored on a lower surface of a cramp block vertically movable against the base block above the base block, the bore being engaged with the cassette-fixing pin, and the connection means has a structure to press the cramp block to the base block side; and that an adjusting screw is aligned for adjusting a distance (gap) between the tool cassette and the base block on the rear surface of the tool cassette and/or on the front surface of the base block.

DESCRIPTION OF THE PREFERRED EMBODIMENTS

The dental automatic cutting apparatus according to the present invention is described in detail with reference to the following embodiments.

Figure 1:
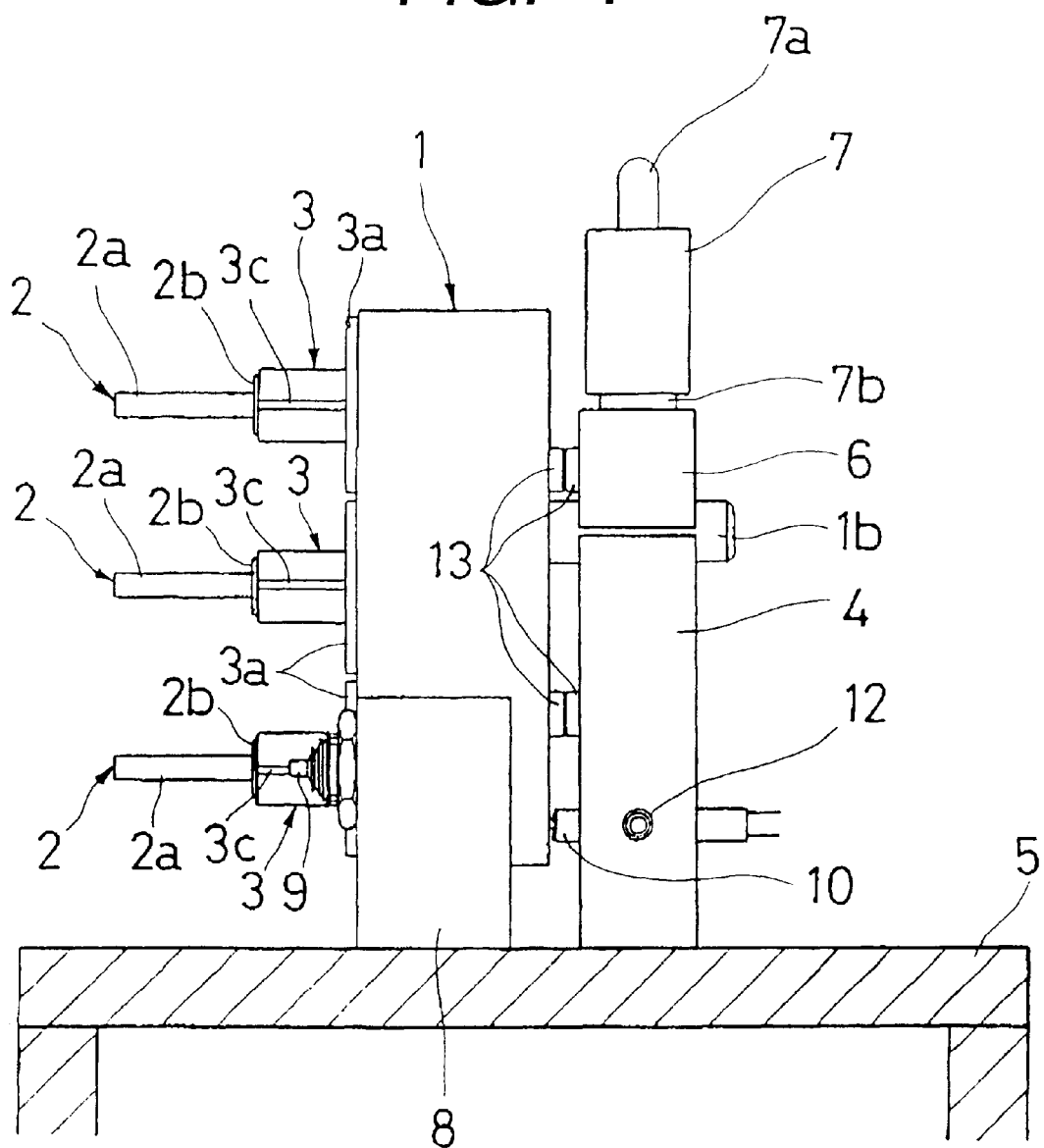
FIG. 1 is an explanatory side view to explain one embodiment of a construction in a state in which a tool cassette is fixed to a base block aligned in a main body of a dental automatic cutting apparatus according to the present invention.
Figure 2:
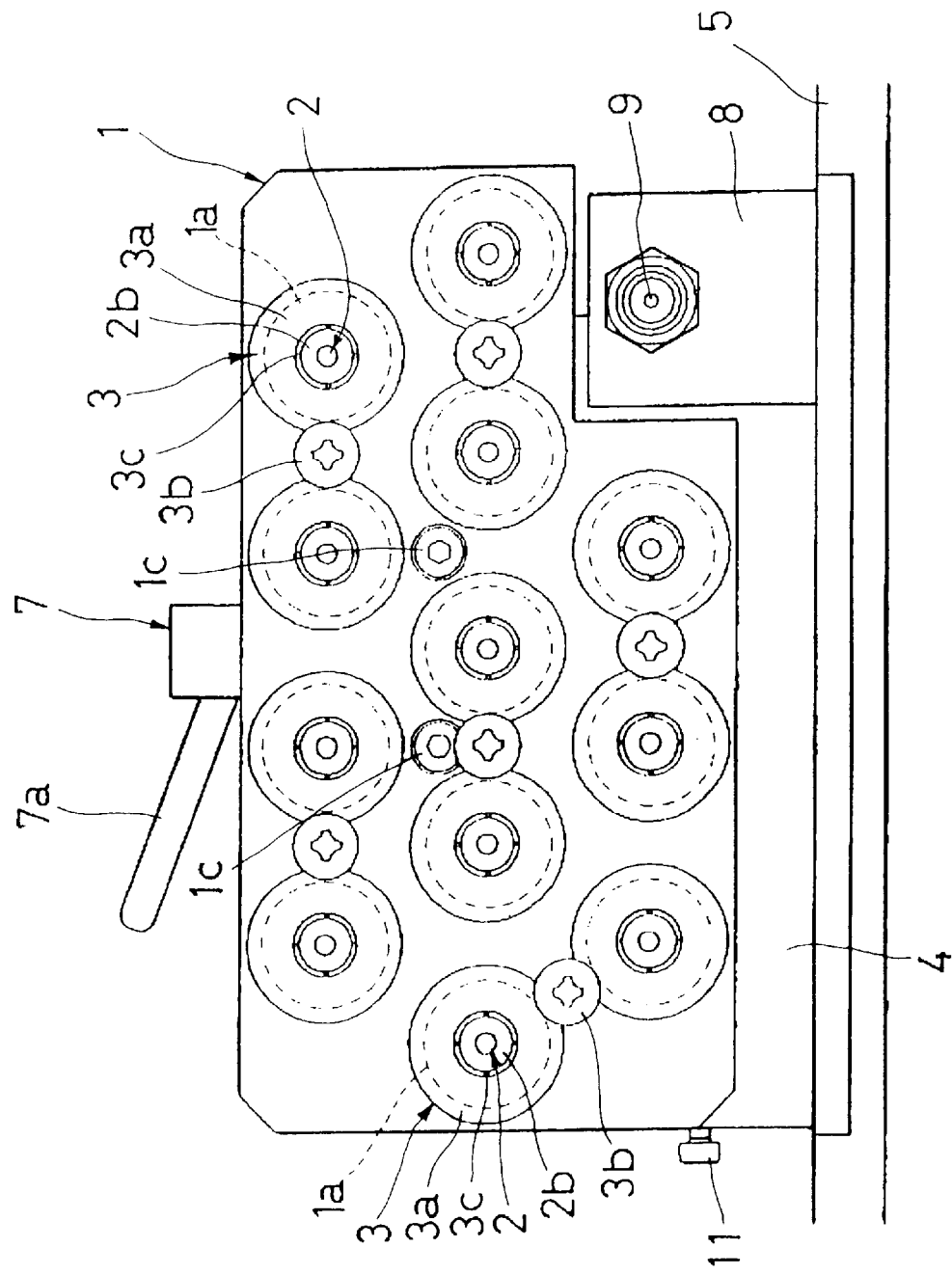
FIG. 2 is an explanatory front view of the embodiment shown in FIG. 1.
Figure 3:
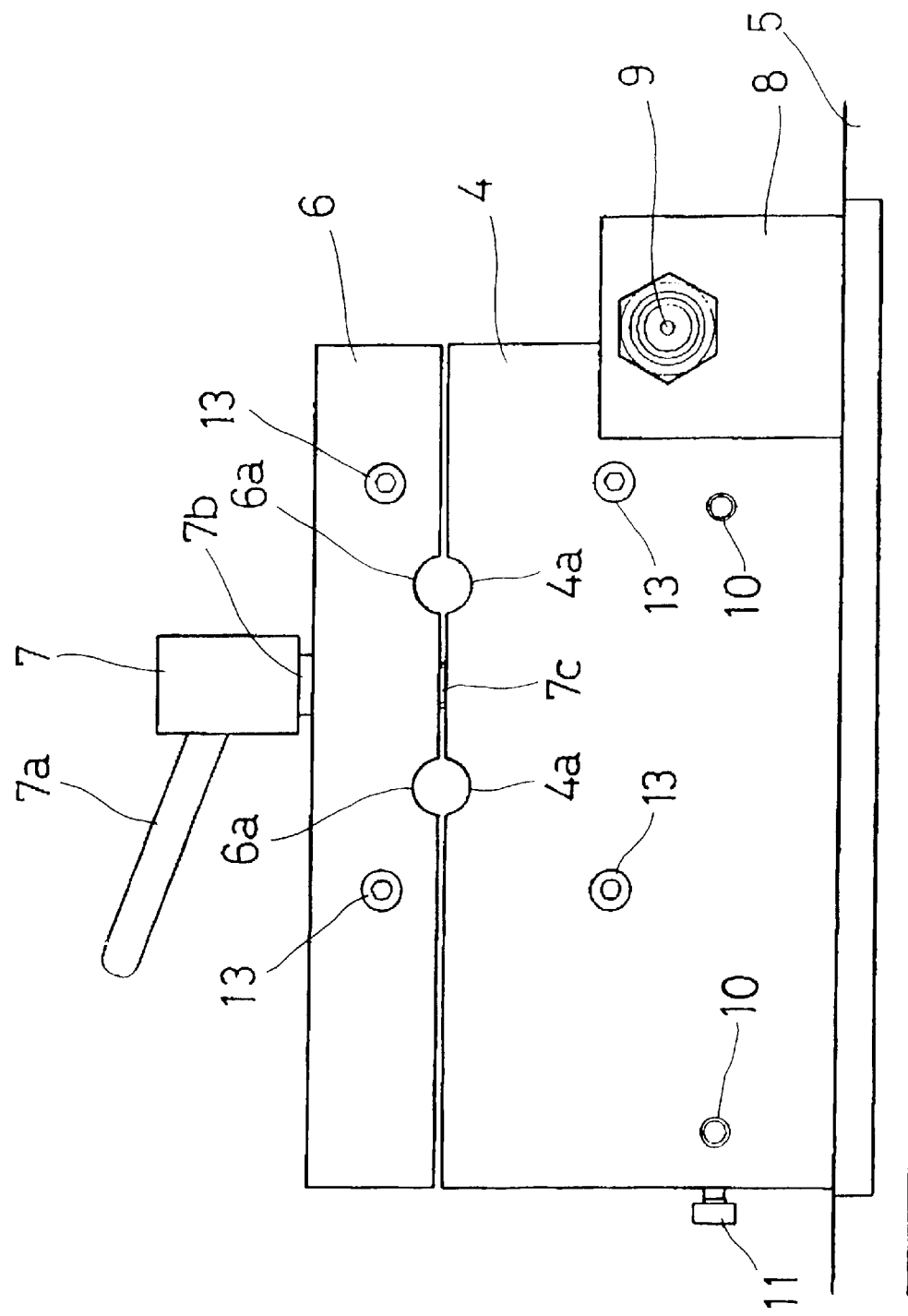
FIG. 3 is an explanatory front view to explain the base block in which the tool cassette is taken out in the embodiment as shown in FIG. 1 and a circumferential construction thereof.

FIG. 1 is an explanatory side view to explain one embodiment of a construction in a state in which a tool cassette is fixed to a base block aligned in a main body of a dental automatic cutting apparatus according to the present invention; FIG. 2 is an explanatory front view of the embodiment shown in FIG. 1; FIG. 3 is an explanatory front view to explain the base block in which the tool cassette is taken out in the embodiment as shown in FIG. 1 and a circumferential construction thereof; and FIG. 4 is an explanatory enlarged slant view to show an embodiment in which a concave for cassette discrimination is aligned in a corner in a lower side on a rear surface of the tool cassette.

Figure 4:
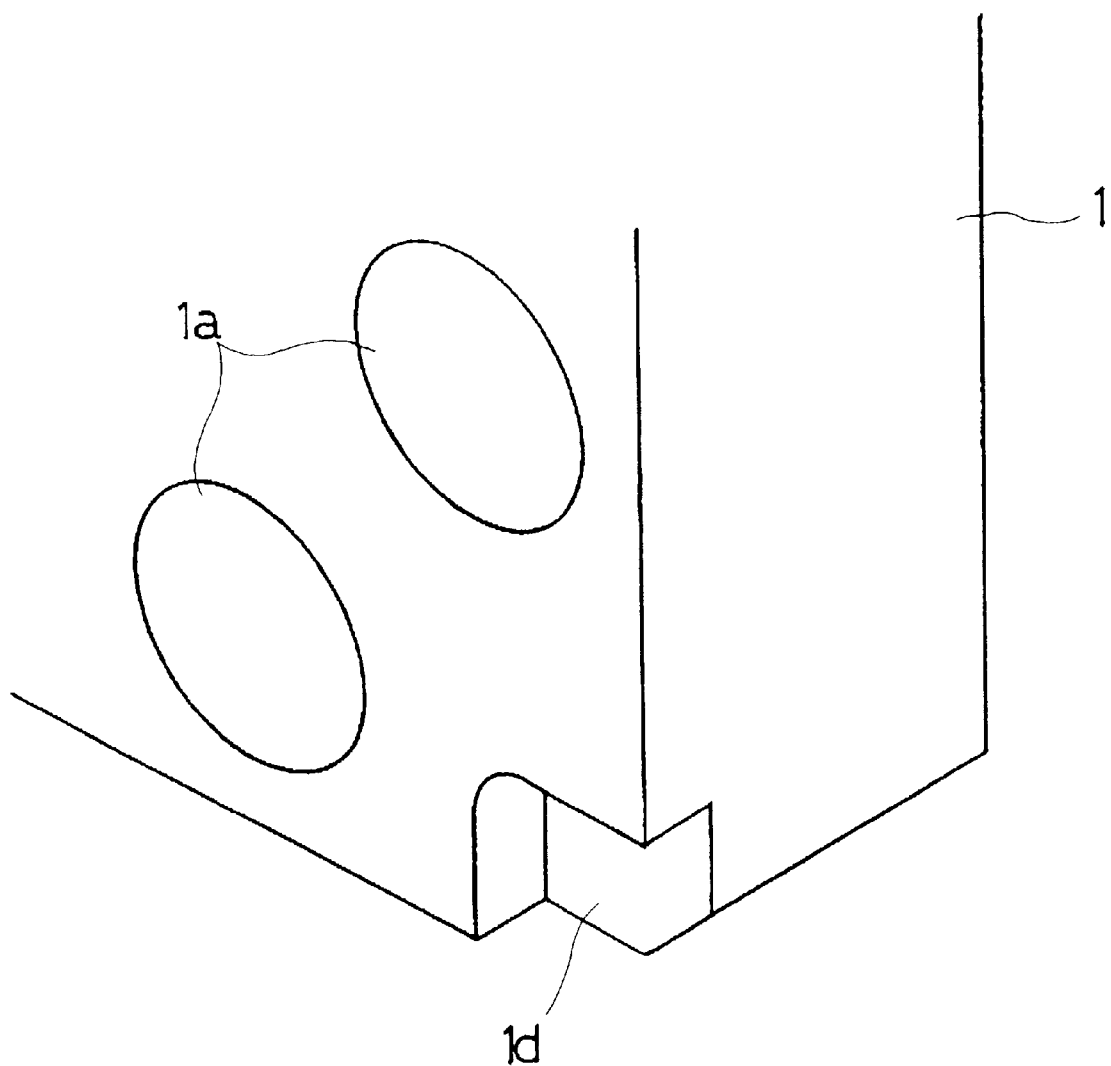
FIG. 4 is an explanatory enlarged slant view to show an embodiment in which a concave for cassette discrimination is aligned in a corner in a lower side on a rear surface of the tool cassette.

In the drawings, a numeral 1 is a metallic tool cassette, in a front surface side of which is provided with at least two tool post-inserting bores 1a having a predetermined size, as shown in FIG. 4. And, the metallic tool cassette 1 is approximately in an L-shape having a notch in a right-hand lower portion thereof, and front and rear surfaces thereof are in parallel to each other and are each made flat, as shown in FIG. 2. In this connection, the tool post-inserting bores 1a have a size (diameter) of from about 15 to 25 mm, and, as shown in FIG. 2, when from about ten to fifteen tool post-inserting bores 1a are aligned in two or three rows, it is possible to set up a necessary number of cutting tools as expected, and it is not necessary to frequently exchange the cutting tool. Accordingly, such is preferred from the standpoint of convenience for use. Further, since it is preferred that the front surface of the tool cassette 1 is perpendicular to the tool post-inserting bores 1a from the standpoint of the operation as described later, the tool cassette 1 preferably has a thickness of from 20 to 30 mm from the convenience for ensuring a retention strength of a tool post 3 as described later.

In the embodiment as shown in the drawings, two cassette-fixing pins 1b, 1b that are a rod-like member as the engagement means extending outwardly are provided in parallel to each other on the rear surface of the tool cassette 1. The cassette-fixing pin 1b is fixed to the tool cassette 1 by a cassette-fixing pin set screw 1c that is penetrated from the front surface side of the tool cassette 1 and screwed. When the two cassette-fixing pins 1b, 1b are connected by connection means provided with a base block 4 and a cramp block 6 as described later, the tool cassette 1 is fixed and held in a predetermined position.

A numeral 2 is a cutting tool for which various variations in shape are prepared as a cutting edge part (not shown). In FIG. 1, only a handle part 2a of the cutting tool 2 is aligned and protruded outwardly from the front surface of the tool cassette 1. This is made in order to grip the handle part 2a by a chuck (not shown) of a spindle of the processing apparatus that has been moved by automatic control mechanism. Accordingly, usually, the cutting edge part is positioned on the tool cassette 1.

And, when the cutting tool 2 is used properly depending upon a difference of dental prosthetic materials subjected to the cutting as described above, the efficiency is high. In other words, for cutting of dental ceramics and dental composite resins, use of a diamond cutter is preferred. On the other hand, for cutting of dental metals, particularly cutting of dental titanium alloys, use of a carbide cutter is preferred.

In addition, to use properly the shape of the cutting edge part depending upon the shape to be cut out by cutting enables to perform processing with a good precision and efficiently. Therefore, there is a background that various types of cutting tools are prepared. In this meaning, it is preferred to prepare the cutting tools 2 having various shapes in the cutting edge part on one's account. However, this case involves a problem that the cost is high. Thus, various commercially available products are made possible for use as the cutting tool 2. However, since the thickness of the handle part 2a of the cutting tool 2 is varied, there is another problem that the cutting tool 2 cannot be accommodated and held in a stable state in the tool cassette 1.

In order to overcome this problem, for the purpose of firmly gripping the cutting tool 2 by the tool post 3 as described later, a synthetic resin-made retention ring 2b is set in the handle part 2a of the cutting tool 2. In other words, each of the retention rings 2b having a constant outer diameter is previously provided with a throughhole having a varied size (diameter), and the retention ring 2b having a throughhole fitting to the thickness of the handle part 2a of the cutting tool 2 to be used is set in advance on the handle part 2a of the cutting tool 2. Thus, not only the trouble for exchanging the tool post 3 every time can be avoided, but also the retention ring 2b is inexpensive so that one can be entitled to a merit from the standpoint of cost. Further, since the chuck of the spindle grips the handle part 2a of the cutting tool 2, the handle parts 2a having a varied thickness can be applied. Accordingly, even when the retention ring 2b is set on the handle part 2a between the portion to be gripped by the chuck of the spindle and the cutting edge part, there is no problem at all.

A numeral 3 is a tool post having a function to accommodate and hold the cutting tool 2, in which a rear side thereof is inserted into the tool post-inserting bore 1a in a good fitting state; a post flange 3a having an outer diameter larger than the diameter of the tool post-inserting bore 1a is provided in a middle portion thereof; and two to four slots 3c are bored from a front end thereof to the post flanges 3a. The tool post 3 is provided with a bore slightly smaller than the outer diameter of the retention ring 2b. In the case where the retention ring 2b is inserted, since it enlarges the slots 3c, the retention ring 2b can be surely gripped utilizing its elasticity.

Further, it is preferred that an opening at the tip of the tool post 3 is opened outwardly in a funnel-like state such that the retention ring 2b is easily inserted. Moreover, in order to fix the tool post 3 to the tool cassette 1, a post set screw 3b is used. In other words, as shown in FIG. 2, a screw hole (not shown) having a predetermined size is previously provided in a middle position between the adjacent two tool post-inserting bores 1a, and the post set screw 3b is screwed into this screw hole, thereby fixing the two tool posts 3, 3 at a top of the post set screw 3b at one time.

A numeral 4 is a base block in which, in particular, a front surface (in the side of the tool cassette 1) thereof is fixed vertically to an apparatus main body 5. One of the reasons why the base block 4 is aligned in such a way may become an important factor in a positional relation with the chuck of the spindle. A detail explanation of this reason will be made in the description with respect to the exchange of the cutting tool 2 as given later. An upper surface of the base block 4 is bored with two grooves 4a, 4a having a cross-section in a semicircle-like state for constructing engagement means to be engaged with the cassette-fixing pins 1b, 1b that are rod-like members as the engagement means, as provided in the tool cassette 1.

A numeral 6 is a cramp block having a lower surface in parallel to the upper surface of the base block 4 and bored with a throughhole (not shown) penetrating vertically in a middle portion thereof and with a cylindrical concave larger than the diameter of the throughhole above the throughhole. And, on a lower surface of the cramp block 6 and in a position corresponding to the location of the two grooves 4a, 4a bored on the upper surface of the base block 4, are bored two grooves 6a, 6a having a cross-section in a semicircle-like state for constructing engagement means to be engaged with the cassette-fixing pins 1b, 1b that are rod-like members as the engagement means, as provided in the tool cassette 1. The grooves 6a, 6a are combined with the grooves 4a, 4a to form round bores. The above-described cassette-fixing pins 1b, 1b are inserted into and engaged with the thus formed round bores.

As the connection means for connecting the cassette-fixing pins 1b, 1b that are rod-like members as the engagement means, as provided in the tool cassette 1, to the engagement means constructed by the two grooves 4a, 4a bored on the upper surface of the base block 4 and the two grooves 6a, 6a bored on the lower surface of the cramp block 6 in an engagement state, is used one having a construction in which a screw hole (not shown) is provided in the base block 4 in a position corresponding to the throughhole of the cramp block 6, and at an upper end of a cramp screw 7c to be screwed into this screw hole is fixed a cylindrical cramp flange 7b on a lower surface of a cramp bar 7 provided with a lever 7a in a side surface thereof, which is set in a free state in the cylindrical concave bored on the upper surface of the cramp block 6.

Specifically, when the cramp bar 7 is horizontally rotated while gripping the lever 7a, the cramp screw 7c, which has been penetrated into the throughhole of the cramp block 6 in advance, is screwed into the screw hole of the base block 4. Then, the cylindrical cramp flange 7b provided on the lower surface of the cramp bar 7 is set in a free state in the cylindrical concave bored on the upper surface of the cramp block 6, whereby the cramp block 6 becomes in a state that it cannot move in both of the longitudinal and crosswise directions, while it can rotate at that position. In such a state, the cramp block 6 is slightly lifted up, and the two cassette-fixing pins 1b, 1b that are rod-like members as the engagement means as provided in the tool cassette 1, are inserted into and engaged with the engagement means constructed by the two grooves 4a, 4a bored on the upper surface of the base block 4 and the two grooves 6a, 6a bored on the lower surface of the cramp block 6. Then, the cramp bar 7 is horizontally rotated while gripping the lever 7a, thereby firmly screwing the cramp screw 7c into the screw hole of the base block 4 and connecting the two cassette-fixing pins 1b, 1b as the engagement means provided in the tool cassette 1 to the base block 4. Thus, the tool cassette 1 can be fixed to the base block 4 in a freely detachable state via the cassette-fixing pins 1b, 1b, while maintaining a desired positional relation.

In the above-described construction, there maybe employed a modification in which one of the two cassette-fixing pins 1b, 1b as the engagement means as aligned in the tool cassette 1 and the base block 4 as well as the cramp block 6 is replaced by one vertically provided on the front surface of the base block 4, and a bore for engaging one of the other engagement means constructed by the two grooves 4a, 4a bored on the upper surface of the base block 4 and the two grooves 6a, 6a bored on the lower surface of the cramp block 6 by the cassette-fixing pin 1b replaced in the rear surface side of the tool cassette 1 is provided. In this case, the replaced cassette-fixing pin 1b can be screwed into and fixed to a portion protruding from the rear surface of the base block 4 using a nut.

A numeral 8 is a touch sensor block, a front surface of which is provided vertically to the apparatus main body 5. In a predetermined position of an upper portion of the front surface of the tough sensor block 8 is installed a touch sensor 9 for gripping the cutting tool 2 by the chuck of the spindle and recognizing a length from the front end surface of the chuck to the front end of the cutting tool 2 as a movement distance of the chuck. In the action for this, after gripping the cutting tool 2 by the chuck, the cutting tool 2 is moved with chuck to bring the tip of the cutting tool 2 into contact with the touch sensor 9, and a computer incorporated in the apparatus main body grasps and digitizes a three-dimensional movement in the X-axis, Y-axis and Z-axis and stores the whole. At this time, needless to say, it is confirmed by this contact that the cutting tool 2 is surely gripped.

A numeral 10 is at least one proximity sensor to be aligned in a predetermined position on the surface of the base block 4 at which the tool cassette 1 is fixed. The reason why the proximity sensor 10 is aligned is explained hereunder. That is, in the case that the number of the proximity sensors 10 is two, the added proximity sensor 10 is aligned for confirming whether the tool cassette 1 has been installed, and the remaining one proximity sensor 10 as a basic alignment differentiates the type of the tool cassette 1. The reason why this differentiation is needed resides in the matter that the cutting tool 2 is used properly depending upon a difference of the material subjected to the cutting. In other words, which of a diamond cutter or a carbide cutter is to be used as the proper cutting tool 2 is already discussed above.

And, the tool cassette 1 is set up exclusively for each cutter, and in a lower side end on the rear surface of one tool cassette 1 is bored a concave 1d for cassette discrimination as a notch, as shown in FIG. 4. This is, for example, made exclusive for use of a cemented carbide cutter. In this connection, the proximity sensor 10 is installed in the base block 4 such that it is positioned in the position at which the concave 1d for cassette discrimination is bored. Thus, for example, when two proximity sensors 10 are aligned, in the case where signals are received from the both proximity sensors 10, the apparatus does confirm that the tool cassette 1 of a diamond cutter has been fixed in the desired position; and on the other hand, in the case where a signal comes from only one of the proximity sensors 10, the apparatus does confirm that the tool cassette 1 of a cemented carbide cutter has been fixed in the desired position. Such a construction is preferred because mismatch between the material subject to the cutting and the cutting tool 2 can be prevented from occurring.

A numeral 13 is an adjusting screw aligned in four pairs, in which four for the tool cassette 1, two for the base block 4 and two for the cramp block 6 are butted each other, respectively, as shown in FIG. 1 and FIG. 3. When the protruding length of the adjusting screw 13 is adjusted, the application to the tool cassettes 1 having a different thickness becomes possible, and hence, it is possible to apply it to the cutting tools 2 having a different length. Further, the rear end of the handle part 2a of the cutting tool 2 can be disposed in substantially the same position whenever the cutting tool 2 is used.

Further, in the case where the position of the tool cassette 1 is adjusted using the adjustment screws 13, a new problem that the positional relation with the proximity sensor 10 cannot be maintained as it is possibly occurs. Namely, a distance between the tool cassette 1 and the proximity sensor 10 is too wide. Hence, a phenomenon in which, nevertheless the tool cassette 1 has been set, the proximity sensor 10 does not transmit a signal possibly occurs. In order to prevent such a phenomenon from occurring, the positional adjustment of the proximity sensor 10 in the left-hand side facing the front is carried out using a proximity sensor position adjusting screw 11 (see FIGS. 2 and 3); and the positional adjustment of the proximity sensor 10 in the right-hand side is carried out using a proximity sensor set screw 12 (see FIG. 1).

Finally, the detachment (exchange) of the cutting tool 2 by automatic control mechanism, namely how the cutting tool 2 accommodated in the tool cassette 1 is set in or taken out from the chuck, is explained hereunder. That method is roughly classified into the following two modes. One mode is a method that is an advantageous mechanism for a small-sized apparatus, in which the chuck itself is moved based on the coordinates of a processing apparatus previously digitized in a three-dimension state in the X-axis, Y-axis and Z-axis. This method is an optimum method for practice in a state that the apparatus main body is made small in size as far as possible, as in the case of the invention in which the subject to the cutting processing is limited to a dental prosthesis. Another mode is a method in which a movement type arm (not shown) is used, the movement of the arm is grasped as a three-dimensional space as in the movement of the chuck as described above, and all of the cutting tools 2 are coordinated and stored in the apparatus. In this case, though a plurality of the tool cassettes 1 are disposed and used, there is a defect that the apparatus itself becomes inevitably large in size.

As described above, the dental automatic cutting apparatus according to the present invention is particularly optimum for a small-sized cutting apparatus in a processing process of dental prostheses such as crowns and inlays by CAD/CAM.

In other words, what the apparatus is made small in size has hitherto involved the following adverse influences. That is, it was impossible to prepare in advance a number of cutting tools and exchange the cutting tool; and the complicated works for exchanging the cutting tool inhibited complete automation of the machine. However, according to the dental automatic cutting apparatus of the present invention, when a worker sets a necessary number of cutting tools as expected in predetermined tool cassettes in advance and installs the box in a predetermined installing position on the processing apparatus, it has become possible to automatically realize a construction in which by automatic control mechanism aligned in the apparatus, necessary cutting tools are automatically taken out from the box and gripped by the chuck of the spindle, and detached too, according to the expected processing order. And, needless to say, even in the processing apparatus in a mode in which a chuck is set in advance every cutting tool, as developed in:recent years, the invention is applicable.

In addition, at the same time, for carrying out precisely the gripping state of the cutting tool by the chuck of the spindle, the tool cassette and the cutting tool can be always positioned in the same position, and the exchange of a set of cutting tools can be easily achieved by the detachment of the tool cassette.

In the light of the above, the dental automatic cutting apparatus according to the present invention is greatly valuable in contributing to an improvement in the technology in the dental remedy.

While the invention has been described in detail and with reference to specific embodiments thereof, it will be apparent to one skilled in the art that various changes and modifications can be made therein without departing from the spirit and scope thereof.

What is claimed is:

1. A dental automatic cutting apparatus having a construction in which cutting tools are made automatically detachable to a chuck and a tool cassette by automatic control mechanism comprising: an engagement means provided to the tool cassette and a base block to maintain to maintain the tool cassette in a detachable manner to the base block to a desired position relation, the tool cassette provided on its front surface side with at least two post-inserting bores through which each tool post having a function to accommodate and hold the cutting tool which can be inserted, and the base block is fixed to a main body of the dental automatic cutting apparatus; and a connection means for connecting the engagement means is provided in the tool cassette to the base block to fix the tool cassette, wherein the engagement means is a bore formed by combining a cassette-fixing pin extending outwardly from a rear surface side of the tool cassette, a groove bored on an upper surface of the base block, and a groove bored on a lower surface of a cramp block vertically movable against the base block above the base block, the bore being engaged with the cassette-fixing pin, and the connection means has a structure to press the cramp block to the base block side.

2. A dental automatic cutting apparatus as claimed in claim 1, wherein at least one proximity sensor is aligned in a predetermined position on the base block in the side to which the tool cassette is fixed, and the proximity sensor discriminates the type of a signal imparted to the fixed tool cassette.

3. A dental automatic cutting apparatus as claimed in any one of claim 1 or 2, wherein an adjusting screw is aligned for adjusting a distance (gap) between the tool cassette and the base block on a rear surface of the tool cassette and/or on a front surface of the base block.

* * * * *

UNITED STATES PATENT AND TRADEMARK OFFICE
CERTIFICATE OF CORRECTION

PATENT NO.    : 6,589,144 B1
DATED         : July 8, 2003
INVENTOR(S)   : Ebihara et al.

It is certified that error appears in the above-identified patent and that said Letters Patent is hereby corrected as shown below:

<u>Title page,</u>
Item [30], Foreign Application Priority Data, should read -- [30]      Foreign Application Priority Data

Sep. 14, 1999  (JP) ............................ 11-260983 --

Signed and Sealed this

Fourteenth Day of October, 2003

JAMES E. ROGAN
*Director of the United States Patent and Trademark Office*